(12) United States Patent
Tanikawa et al.

(10) Patent No.: US 11,266,814 B2
(45) Date of Patent: Mar. 8, 2022

(54) SUPPORT CATHETER

(71) Applicant: NIPRO CORPORATION, Osaka (JP)

(72) Inventors: Masahiro Tanikawa, Osaka (JP); Hidenobu Akihama, Osaka (JP)

(73) Assignee: NIPRO CORPORATION, Osaka (JP)

( * ) Notice: Subject to any disclaimer, the term of this patent is extended or adjusted under 35 U.S.C. 154(b) by 330 days.

(21) Appl. No.: 16/317,894

(22) PCT Filed: Jul. 14, 2017

(86) PCT No.: PCT/JP2017/025745
§ 371 (c)(1),
(2) Date: Jan. 15, 2019

(87) PCT Pub. No.: WO2018/030075
PCT Pub. Date: Feb. 15, 2018

(65) Prior Publication Data
US 2020/0338315 A1    Oct. 29, 2020

(30) Foreign Application Priority Data

Aug. 10, 2016  (JP) ............................. JP2016-157870

(51) Int. Cl.
*A61M 25/00*   (2006.01)
*A61M 25/06*   (2006.01)
*A61M 25/02*   (2006.01)

(52) U.S. Cl.
CPC . *A61M 25/0662* (2013.01); *A61M 2025/0004* (2013.01); *A61M 2025/028* (2013.01); *A61M 2025/0253* (2013.01)

(58) Field of Classification Search
CPC .... A61M 2025/0253; A61M 2025/004; A61M 2025/0183; A61M 2025/0175
See application file for complete search history.

(56) References Cited

U.S. PATENT DOCUMENTS 5,439,445 A * 8/1995 Kontos .................. A61F 2/88
                                                      604/103.1
6,447,479 B1   9/2002 Nobuyoshi et al.
(Continued)

FOREIGN PATENT DOCUMENTS

JP       2000-107293 A    4/2000
JP       2000107293 A  *  4/2000   .......... A61M 25/104
(Continued)

OTHER PUBLICATIONS

Kumoyama Kenichi; Mineo Shigeyuki; Nobeyoshi Masakiyo; Takahashi Giichi, Vasodilating Instrument, Apr. 18, 2000, ESPACENET machine translated JP2000107293A, See prior art rejection for pertinent pages (Year: 2000).*
(Continued)

*Primary Examiner* — Bhisma Mehta
*Assistant Examiner* — Robert F Allen
(74) *Attorney, Agent, or Firm* — Alleman Hall Creasman & Tuttle LLP

(57) ABSTRACT

A support catheter is used together with a guiding catheter in which a treatment catheter is inserted, the guiding catheter guiding the treatment catheter in a blood vessel, the support catheter being inserted in the guiding catheter from a proximal-side opening of the guiding catheter and having such a length that the support catheter protrudes from a distal-side opening of the guiding catheter, the support catheter guiding a distal end portion of the treatment catheter to a treatment site. The support catheter includes: a distal shaft forming a distal-side portion of the support catheter, the distal shaft having a tubular shape such that the treatment catheter is insertable in the distal shaft; and a proximal shaft forming a proximal-side portion of the support catheter. The proximal shaft is joined to a proximal-side portion of the distal shaft by a modified polyolefin-based adhesive.

6 Claims, 5 Drawing Sheets

(56) References Cited

U.S. PATENT DOCUMENTS

| 7,695,491 B2* | 4/2010 | Clubb ........................ 606/200 |
| 10,980,987 B2* | 4/2021 | Tarunaga .......... A61M 25/0028 |
| 2014/0276618 A1 | 9/2014 | Di Caprio et al. |

FOREIGN PATENT DOCUMENTS

| JP | 2011135989 A | * | 7/2011 | |
| JP | 2012-135379 A | | 7/2012 | |
| JP | 2012135379 A | * | 7/2012 | ........ A61M 25/0662 |
| JP | 5392566 B2 | | 1/2014 | |
| JP | 2016517320 A | | 6/2016 | |

OTHER PUBLICATIONS

Kameoka Koji, Slave Catheter, Jul. 19, 2012, ESPACENET machine translated JP2012135379A, See prior art rejection for pertinent pages (Year: 2012).*

Tanigawa Masahiro, Monorail Type Catheter, Jul. 14, 2011, ESPACENET machine translated JP2011135989A, See prior art rejection for pertinent pages (Year: 2011).*

* cited by examiner

SUPPORT CATHETER

TECHNICAL FIELD

The present invention relates to a rapid-exchange-type support catheter that is used together with a treatment catheter and a guiding catheter and that guides the treatment catheter to a treatment site.

BACKGROUND ART

In percutaneous coronary intervention (PCI), there are cases where a support catheter is used together with a treatment catheter and a guiding catheter. One of the known support catheters is, for example, a catheter disclosed in Patent Literature 1. The catheter of Patent Literature 1 includes an insertion tube and a wire. The wire has, at its extending distal end, a hook-shaped portion that is bent in a U shape. The hook-shaped portion is placed on the outer peripheral surface of the insertion tube, and the outer peripheral surface of the insertion tube is covered by a cover tube. The cover tube is made of a thermally shrinkable material. The cover tube is, by being thermally shrunk, tightly wrapped around the insertion tube. In this manner, the wire is sandwiched between the two tubes and fixed to the outer peripheral surface of the insertion tube.

CITATION LIST

Patent Literature

PTL 1: Japanese Patent No. 5392566

SUMMARY OF INVENTION

Technical Problem

In the case of performing femoral region approach by using the catheter of Patent Literature 1, a joint portion of the catheter where the insertion tube and the wire are joined together becomes bent when the distal end of the catheter is pushed into a stenosis site in a coronary artery. When the catheter of Patent Literature 1 in such a bent state is repeatedly pushed and pulled with a clearance being formed between the catheter of Patent Literature 1 and a guiding catheter in which the catheter of Patent Literature 1 is inserted, the hook-shaped portion slides between the two tubes, and as a result, push-in force is not efficiently transmitted between the wire (a proximal shaft) and the insertion tube (a distal shaft).

In view of the above, an object of the present invention is to provide a support catheter that makes it possible to suppress the occurrence of a situation where the push-in force is not efficiently transmitted from the proximal shaft to the distal shaft when the support catheter is pushed and pulled repeatedly.

Solution to Problem

A support catheter according to the present invention is used together with a guiding catheter in which a treatment catheter is inserted, the guiding catheter guiding the treatment catheter in a blood vessel, the support catheter being inserted in the guiding catheter from a proximal-side opening of the guiding catheter and having such a length that the support catheter protrudes from a distal-side opening of the guiding catheter, the support catheter guiding a distal end portion of the treatment catheter to a treatment site. The support catheter includes: a distal shaft forming a distal-side portion of the support catheter, the distal shaft having a tubular shape such that the treatment catheter is insertable in the distal shaft; and a proximal shaft forming a proximal-side portion of the support catheter. The proximal shaft is joined to a proximal-side portion of the distal shaft by a modified polyolefin-based adhesive.

According to the present invention, the occurrence of sliding of the proximal shaft against the distal shaft can be suppressed. Accordingly, even when the support catheter is pushed and pulled repeatedly, push-in force can be transmitted from the proximal shaft to the distal shaft, and reduction of the push-in force can be suppressed.

Advantageous Effects of Invention

The present invention makes it possible to suppress the occurrence of a situation where the push-in force is not efficiently transmitted from the proximal shaft to the distal shaft when the support catheter is pushed and pulled repeatedly.

DESCRIPTION OF EMBODIMENTS

Hereinafter, support catheters 1, 1A, and 1B of Embodiments 1 to 3 according to the present invention are described with reference to the drawings. It should be noted that directions mentioned in the description below are used for the sake of convenience of the description, but do not suggest that the orientation and the like of the components of the present invention are limited to such directions. The support catheters 1, 1A, and 1B described below are merely embodiments of the present invention. Therefore, the present invention is not limited to these embodiments, and additions, deletions, and modifications can be made to the embodiments without departing from the spirit of the present invention.

Embodiment 1

Figure 1:
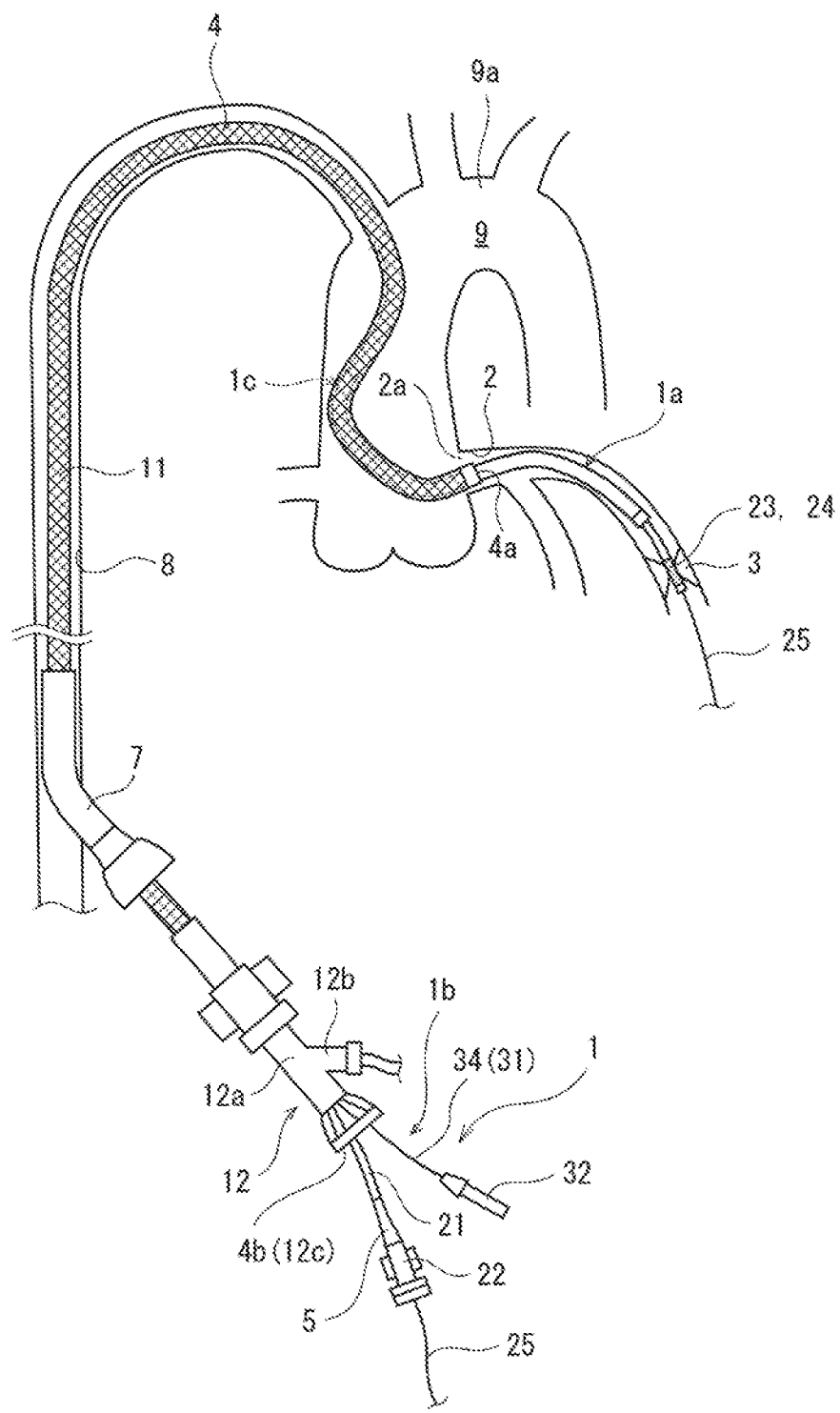
FIG. 1 shows a state where a support catheter of Embodiment 1 of the present invention is used together with a treatment catheter and a guiding catheter.

As a technique for expanding a stenosis site 3 formed in a coronary artery 2 as shown in FIG. 1, percutaneous coronary intervention (PCI) is known, for example. In PCI, a guiding catheter 4, a balloon catheter 5, a support catheter 1, and a guide wire 25 are mainly used.

<Guiding Catheter>

The guiding catheter 4 is a catheter for guiding the balloon catheter 5 and the support catheter 1 in a blood vessel, and the guiding catheter 4 is inserted into, for example, a radial artery 8 or a femoral artery (not shown) by using a sheath 7 described below. The guiding catheter 4 includes a guiding catheter body 11 and a Y-shaped connector 12. The guiding catheter body 11 is in the shape of an elongated tube, and is configured such that the balloon catheter 5 and the support catheter 1 are insertable in the guiding catheter body 11. The guiding catheter body 11 is made of a cylindrical flexible tube that can be curved. Accordingly, the guiding catheter body 11 can be pushed forward through curved blood vessels. The Y-shaped connector 12 is provided on the proximal end portion of the guiding catheter body 11. The Y-shaped connector 12 includes a body 12a and a side arm 12b. A chemical solution or contrast medium can be injected from the side arm 12b. The distal end portion of the body 12a is attached to the proximal end portion of the guiding catheter body 11. The body 12a includes a proximal-side opening 12c formed at the proximal end of the body 12a. The balloon catheter 5 and the support catheter 1 can be inserted into the body 12a through the proximal-side opening 12c.

<Balloon Catheter>

The balloon catheter 5, which is a treatment catheter, is a catheter to be inserted into the stenosis site 3 in the coronary artery for expanding the stenosis site 3. It should be noted that a conventionally known balloon catheter can be suitably adopted as the balloon catheter 5. For example, the balloon catheter 5 is a rapid exchange (RX) type catheter. As shown in FIG. 1, the balloon catheter 5 includes a treatment catheter body 21 and a connector 22. The treatment catheter body 21 is formed in the shape of an elongated tube. In the present embodiment, the treatment catheter body 21 includes, at its distal end portion, a balloon 23 with a stent 24 wrapped around it. It should be noted that a conventionally known stent can be suitably adopted as the stent 24. The balloon catheter 5 is used together with the guide wire 25, the guiding catheter 4, and the support catheter 1.

<Support Catheter>

Figure 2:
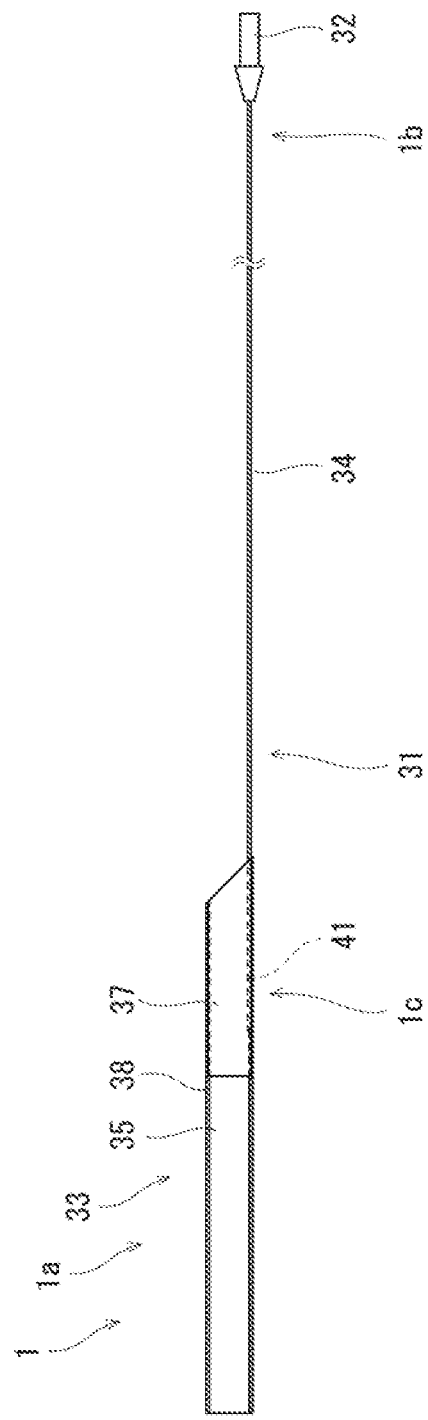
FIG. 2 is a cutaway side view of a cover shaft of the support catheter of FIG. 1.

The support catheter 1 is a catheter for guiding the balloon 23 of the balloon catheter 5 to a position that is closer to the stenosis site 3 than the ostium of the coronary artery 2 is. Specifically, the support catheter 1 guides the balloon 23 to the stenosis site 3. The support catheter 1 also serves to support the balloon 23 when inserting the balloon 23 into the stenosis site 3. The support catheter 1 having these functions includes a support catheter body 31 and a hub 32 as shown in FIG. 2. The support catheter body 31 includes a distal shaft 33 and a proximal shaft 34. The distal shaft 33 has a roughly cylindrical shape, and the balloon catheter 5 is insertable in the distal shaft 33. The distal shaft 33 thus configured forms a distal-side portion 1a of the support catheter 1, and includes a shaft body 35, a cover tube 37, and a cover shaft 38.

The shaft body 35 is formed by a roughly cylindrical member with a three-layer structure having an inner layer, a reinforcement layer, and an outer layer. The inner layer is made of, for example, polytetrafluoroethylene (PTFE) or tetrafluoroethylene-perfluoroalkylvinyl ether copolymer (PFA). The outer layer is made of, for example, a polyamide blended with a contrast medium or a polyamide elastomer (in the present embodiment, polyether block amide (Pebax (registered trademark) available from Arkema)). It should be noted that both the inner layer and the outer layer may be made of the same material, which is not limited to the aforementioned materials. A mesh-like roughly cylindrical member made of stainless steel is embedded between the inner layer and the outer layer. The mesh-like cylindrical member forms the reinforcement layer. The outer peripheral surface of the shaft body 35 is coated with a hydrophilic polymer that contains, for example, polyurethane or polyvinyl pyrrolidone (PVP). The proximal shaft 34 is attached to the outer peripheral surface of the thus-configured shaft body 35.

The proximal shaft 34 is an elongated wire rod made of, for example, stainless steel, and the surface thereof is coated with PTFE. The proximal shaft 34 is provided with the hub 32 at its proximal end portion. The hub 32 is a columnar member made of, for example, a polyamide elastomer so that a surgeon can hold the hub 32 with their fingers. The proximal shaft 34 thus configured forms a proximal-side portion 1b of the support catheter 1. A distal end portion 41 of the proximal shaft 34 is attached to the outer peripheral surface of a proximal-side portion of the distal shaft 33.

Figure 3:
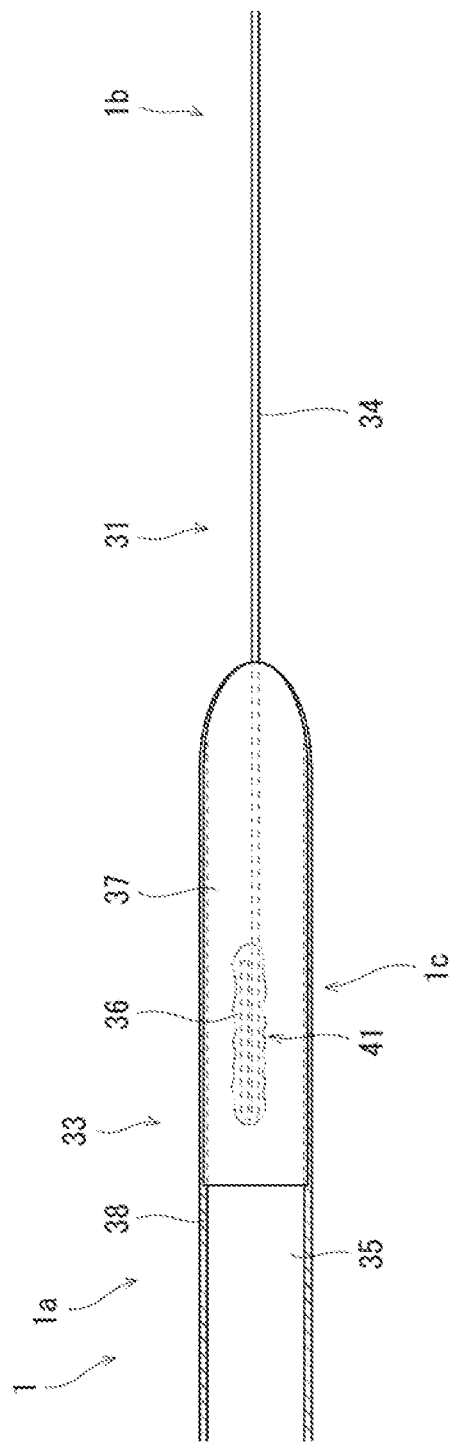
FIG. 3 is an enlarged bottom view of a joint portion where a proximal shaft and a distal shaft of the support catheter of FIG. 2 are joined together.

To be more specific, the proximal shaft 34 is bent back at its distal end as shown in FIG. 3. A portion forward of the bent-back distal end and a portion rearward of the bent-back distal end (i.e., a portion forward of the bending-back point and a portion rearward of the bending-back point) are adjacent to each other. In this manner, the distal end portion 41 of the proximal shaft 34 is hook-shaped (or U-shaped). The distal end portion 41 having such a shape is disposed on the outer peripheral surface of the shaft body 35 so as to extend along the outer peripheral surface, and the entire distal end portion 41 is positioned on the outer peripheral surface of the shaft body 35. An adhesive 36 is applied to (placed on) the distal end portion 41 thus disposed, and the distal end portion 41 is fixed (joined) to the outer peripheral surface of the shaft body 35 by the adhesive 36.

The adhesive 36 is, for example, a modified polyolefin-based adhesive (preferably an adhesive containing chlorinated polypropylene). The modified polyolefin-based adhesive is an adhesive containing a thermoplastic modified polyolefin as an adhesive component, and known examples of the modified polyolefin-based adhesive include a hot melt adhesive and a solvent-based adhesive. For example, in a case where a solvent-based adhesive is adopted, the distal end portion 41 and the outer peripheral surface of the shaft body 35 are adhered together by drying the adhesive at a high temperature. Generally speaking, a modified polyolefin-based adhesive has a molecular structure in which a polar group is introduced as, for example, a side chain or substituent into low-polarity or nonpolar polyolefin resin molecules. Therefore, the modified polyolefin-based adhesive can be adhered well to polyamide resins, such as polyamides and polyamide elastomers, and to stainless steel. It should be noted that the adhesive 36 is not limited to a modified polyolefin-based adhesive. Any adhesive can be used as the adhesive 36, so long as the resin forming the shaft body 35 and stainless steel can be adhered together well by the adhesive.

In a state where the distal end portion 41 is disposed along the outer peripheral surface of the shaft body 35, the adhesive 36 thus configured is applied to the distal end portion 41 and its vicinity on the outer peripheral surface of the shaft body 35. Thereafter, the adhesive 36 is heated at a high temperature (e.g., at 200° C. or higher) and thereby dried. As a result, the adhesive 36 is solidified, and the distal end portion 41 and the outer peripheral surface of the shaft body 35 are adhered together. The outer peripheral surface of the shaft body 35 is covered with the cover tube 37 for the purpose of improving the joint strength between the distal end portion 41 and the shaft body 35.

The cover tube 37 is a roughly cylindrical member made of a thermoplastic resin material, and is externally fitted to the proximal-side portion of the shaft body 35. The cover tube 37 extends longer than the distal end portion 41 in the axial direction, and covers the entire distal end portion 41. Heat is applied to the cover tube 37 when the cover tube 37 having such a shape is in the state of being externally fitted to the shaft body 35. As a result, the cover tube 37 is plastic-deformed (more specifically, thermally shrunk). Consequently, the cover tube 37 is tightly wrapped around the outer peripheral surface of the shaft body 35, and the distal end portion 41 is sandwiched between the shaft body 35 and the cover tube 37. Thereafter, the cylindrical cover shaft 38 is placed over the cover tube 37 to cover the cover tube 37.

The cover shaft 38 is made of, for example, a polyamide or polyamide elastomer. When heat is applied to the cover shaft 38, the cover shaft 38 is plastic-deformed (more specifically, thermally shrunk), and consequently, the cover shaft 38 is tightly wrapped around the cover tube 37. The cover shaft 38 thus configured serves to protect the shaft body 35 and the distal end portion 41 of the proximal shaft 34.

<Method of Using Support Catheter>

Hereinafter, a method of approaching a treatment site from a radial artery in PCI is described with reference to FIG. 1. In this method, the above-described support catheter 1, guiding catheter 4, balloon catheter 5, and guide wire 25 are used. In PCI, first, a surgeon punctures the radial artery 8 with a needle that is not shown, and inserts the sheath 7 into the puncture site. Then, the guiding catheter 4 is inserted into the radial artery 8 through the sheath 7. After being thus inserted, the guiding catheter 4 is pushed forward until a distal-side opening 4a of the guiding catheter 4 reaches an ostium 2a of the coronary artery 2 through an aortic arch 9. When the distal-side opening 4a reaches the ostium 2a, the guide wire 25 is inserted and the support catheter 1 is inserted from a proximal-side opening 4b of the guiding catheter 4. By being pushed and pulled by the surgeon, the support catheter 1 moves forward inside the guiding catheter 4 while being guided by the guide wire 25 until the distal-side portion 1a protrudes from the distal-side opening 4a. In this manner, the distal-side portion 1a of the support catheter 1 is inserted into the coronary artery 2, and then reaches the stenosis site 3.

Each of the radial artery 8 and the aortic arch 9, through which the support catheter 1 is pushed forward as described above, branches and curves. Therefore, the support catheter 1 is bent along the shapes of these arterial ducts, and in the bent state, pushed forward through the arterial ducts. The same is true for a joint portion 1c where the distal shaft 33 and the proximal shaft 34 are joined together. When the support catheter 1 is pushed forward in the bent state, such force as to move the distal shaft 33 and the proximal shaft 34 away from each other is applied to the distal shaft 33 and the proximal shaft 34 at the joint portion 1c.

In the case of the conventional catheter of Patent Literature 1, the insertion tube and the wire are not adhered together. Therefore, when such force as to move the insertion tube and the distal end portion of the wire away from each other is applied to the insertion tube and the distal end portion of the wire, the space between the insertion tube and the cover tube is widened to form a gap. The gap allows the wire to slide between the insertion tube and the cover tube. Accordingly, when the wire is pushed and pulled, the wire slides between the insertion tube and the cover tube, and as a result, the efficiency of push-in force transmission between the insertion tube and the wire is reduced. It should be noted that when such sliding of the wire was repeated in a durability test as described below, the cover tube and the cover shaft covering the cover tube were scraped, and eventually, the wire was exposed. In such a state, the wire was further pushed and pulled repeatedly. Consequently, the distal end portion of the wire stuck out of the cover tube and the cover shaft, and the catheter of Patent Literature 1 ruptured between the insertion tube and the wire.

On the other hand, in the support catheter 1 of the present embodiment, the distal end portion 41 of the proximal shaft 34 and the outer peripheral surface of the shaft body 35 are fixed to each other by the adhesive 36. Therefore, even when the joint portion 1c is bent, the distal end portion 41 and the outer peripheral surface of the shaft body 35 do not move away from each other, and the distal end portion 41 does not slide on the outer peripheral surface of the shaft body 35. Therefore, the push-in force applied to the proximal shaft 34 can be directly transmitted from the distal end portion 41 to the distal shaft 33. Since the distal end portion 41 does not slide on the outer peripheral surface of the shaft body 35, the scraping of the cover tube 37 and the cover shaft 38 can be suppressed. Consequently, even when the proximal shaft is pushed and pulled repeatedly, the occurrence of the following situations can be suppressed: a situation where the distal end portion 41 of the proximal shaft 34 becomes exposed to the outside of the cover tube 37 and the cover shaft 38; and a situation where the distal end portion 41 sticks out of the cover tube 37 and the cover shaft 38, causing separation of the proximal shaft 34 from the distal shaft 33, resulting in rupture of the support catheter 1.

After the distal-side portion 1a of the support catheter 1 is pushed into the stenosis site 3 in the above-described manner, the balloon catheter 5 is inserted from the proximal-side opening 4b of the guiding catheter 4. The distal end portion of the balloon catheter 5 is inserted into the distal shaft 33. Thereafter, the balloon catheter 5 is pushed forward until it protrudes from the distal end of the distal shaft 33. By pushing the balloon catheter 5 forward in this manner, the distal end portion of the balloon catheter 5 is inserted into the stenosis site 3, and the balloon 23 and the stent 24 are positioned at the stenosis site 3. Then, the pushing-in of the balloon catheter 5 is stopped.

While the balloon catheter 5 is being pushed forward in the above-described manner, the distal end portion of the balloon catheter 5 is guided to the ostium 2a of the coronary artery 2 by the guiding catheter 4, and after passing the ostium 2a, the distal end portion of the balloon catheter 5 is guided to the stenosis site 3 by the support catheter 1. Since the distal shaft 33 of the support catheter 1 extends to the stenosis site 3 or the vicinity thereof, the distal end portion of the balloon catheter 5 is supported by the distal end portion of the distal shaft 33 when the distal end portion of the balloon catheter 5 is pushed into the stenosis site 3. Thereafter, the balloon 23 is inflated by a pressure fluid. At the same time, the stent 24 is expanded, and thereby the stenosis site 3 is expanded. This makes it possible to restore the blood flow of the stenosis site 3.

<Durability Test>

Two durability tests as described below were conducted on each of the catheter of Patent Literature 1 (however, the elastic extension portion was not adopted) and the support catheter 1. The first test was a modeling test in which femoral region approach was modeled. The second test was a tensile durability test in which the distal end portion and the middle portion of each catheter were held and pulled in the longitudinal direction of the catheter. In the modeling test, not the above-described radial artery approach but femoral region approach similar thereto was modeled. In the modeling test, first, an aortic arch blood vessel model intended for the femoral region approach was created. Then, in the blood vessel model, each of the catheter of Patent Literature 1 and the support catheter 1 was passed from a descending aorta to an ascending aorta, and pushed into a coronary artery. The insertion tube and the distal shaft 33 were fixed by forceps or the like in a state where the middle portion of the insertion tube and the middle portion of the distal shaft 33 were inserted in the coronary artery. In this manner, the joint portion 1c was positioned in a curved portion 9a of the aortic arch 9. In this state, the catheter of Patent Literature 1 and the support catheter 1 were pushed and pulled repeatedly.

In this modeling test, the following results were obtained. Specifically, the catheter of Patent Literature 1 ruptured when the pushing and pulling of the catheter with a load in the range of not less than 15 N but not greater than 20 N was repeated 3 times or more but not more than 15 times. On the other hand, the support catheter 1 did not rupture even when the pushing and pulling of the support catheter 1 was repeated 50 times or more. That is, it was confirmed that the following advantageous effect was obtained: when the support catheter 1 was pushed and pulled in a state where the joint portion 1c was bent, the occurrence of the sliding was suppressed, and thereby the rupture was suppressed.

In the tensile durability test, the distal end of the catheter of Patent Literature 1 and the distal end of the support catheter 1 were held, and also, a part of the wire and a part of the proximal shaft 34 were held. The part of the wire was away from the distal end of the catheter of Patent Literature 1 by a predetermined length, and the part of the proximal shaft 34 was away from the distal end of the support catheter 1 by the predetermined length. In this state, pulling was repeatedly performed at a predetermined speed (e.g., 500 mm/min) with a predetermined load (e.g., not greater than 15 N), and the durability was evaluated. In the tensile durability test, the following results were obtained. Specifically, the tensile durability test was performed on a plurality of test specimens of the catheter of Patent Literature 1. In all of the test specimens, sliding between the insertion tube and the wire occurred, and all of the test specimens ruptured. It should be noted that the minimum required number of repetitions of the pulling for the rupture to occur was 4 times. The tensile durability test was also performed on a plurality of test specimens of the support catheter 1. None of the test specimens of the support catheter 1 ruptured even after the pushing and pulling was repeated 30 times. That is, the occurrence of sliding between the distal shaft 33 and the proximal shaft 34 was suppressed. Thus, it was confirmed that not only when the joint portion 1c was in a bent state, but also when the joint portion 1c was in a straight state, the aforementioned advantageous effect was obtained at the time of pushing and pulling the support catheter 1.

As described above, since the distal shaft 33 and the proximal shaft 34 are fixed together by the adhesive 36 in the support catheter 1, even when the proximal shaft 34 is pushed and pulled repeatedly, the occurrence of the sliding between the distal shaft 33 and the proximal shaft 34 can be suppressed. This makes it possible to suppress the occurrence of a situation where the push-in force applied to the proximal shaft 34 is not transmitted to the distal shaft 33. That is, the occurrence of the following situation can be suppressed: the support catheter 1 ruptures between the distal shaft 33 and the proximal shaft 34, and thereby the transmission of the push-in force from the proximal shaft 34 to the distal shaft 33 is reduced. Since the occurrence of the sliding between the distal shaft 33 and the proximal shaft 34 can be suppressed, the following situation can be prevented: the cover tube 37 and the cover shaft 38, which are made of fluorocarbon resin, are scraped by the distal end portion 41, and consequently the distal end portion 41 sticks out of the cover tube 37 and the cover shaft 38. This also makes it possible to suppress the occurrence of the situation where the transmission of the push-in force from the proximal shaft 34 to the distal shaft 33 is reduced.

In the support catheter 1, the distal end portion 41 of the proximal shaft 34 is hook-shaped. In the distal end portion 41, the portion forward of the bent-back distal end and the portion rearward of the bent-back distal end are adjacent to each other. The adhesive 36 is applied to the entire distal end portion 41 having such a shape and to the vicinity thereof. The adhesive 36 flows into between the portion forward of the bent-back distal end and the portion rearward of the bent-back distal end, and thereby the area of contact with the distal shaft 33 is large. Therefore, when the proximal shaft 34 is pushed and pulled, the distal end of the proximal shaft 34 is caught in the solidified adhesive 36. This also makes it possible to suppress displacement of the proximal shaft 34 relative to the distal shaft 33. It should be noted that it is not essential that the adhesive 36 be applied not only to the distal end portion 41 but also to the vicinity of the distal end portion 41. Alternatively, the adhesive 36 may be applied only to the distal end portion 41. The adhesive 36 may be applied in various manners. For example, the adhesive may be sprayed onto the distal end portion 41; the distal end portion 41 may be immersed in an adhesive solution; or the adhesive may be applied to the distal end portion 41 with a brush or the like. The manner of applying the adhesive 36 to the distal end portion 41 is not particularly limited.

<Combination of Adhesive and Cover Tube>

As with a conventional monorail catheter, basically, the insertion tube and the wire are fixed together by thermally shrinking the cover tube 37 and thereby tightly wrapping the cover tube 37 around the outer peripheral surface of the insertion tube. However, the inventors of the present invention have discovered at this time that when such manner of fixing is adopted, sliding of the wire against the insertion tube occurs in the above-described particular case. Such technical problem needs to be solved. In order to solve the problem, the inventors of the present invention have come up with: in the support catheter 1, thermally shrinking the cover tube 37 to tightly wrap the cover tube 37 around the outer peripheral surface of the shaft body 35, thereby fixing the distal end portion 41 and the outer peripheral surface of the shaft body 35 together; and in addition, adhering the distal end portion 41 and the shaft body 35 together by using the adhesive 36. Thus, it has been discovered for the first time that, in the above-described particular case, the distal end portion 41 slides against the shaft body 35. In order to overcome this technical problem, the inventors of the present invention have come up with adhering the distal end portion 41 and the shaft body 35 together by using the adhesive 36. This makes it possible to suppress the occurrence of the rupture of the support catheter 1 between the distal shaft 33 and the proximal shaft 34, and suppress the occurrence of the situation where the transmission of the push-in force from the proximal shaft 34 to the distal shaft 33 is reduced.

Embodiment 2

A support catheter 1A of Embodiment 2 is similar in configuration to the support catheter 1 of Embodiment 1. Therefore, the description below regarding the configuration of the support catheter 1A of Embodiment 2 mainly describes differences from the configuration of the support catheter 1 of Embodiment 1. In Embodiment 2, the same configurations as those of Embodiment 1 are denoted by the same reference signs as those used in Embodiment 1, and the description and illustration of such configurations are omitted.

Figure 4:
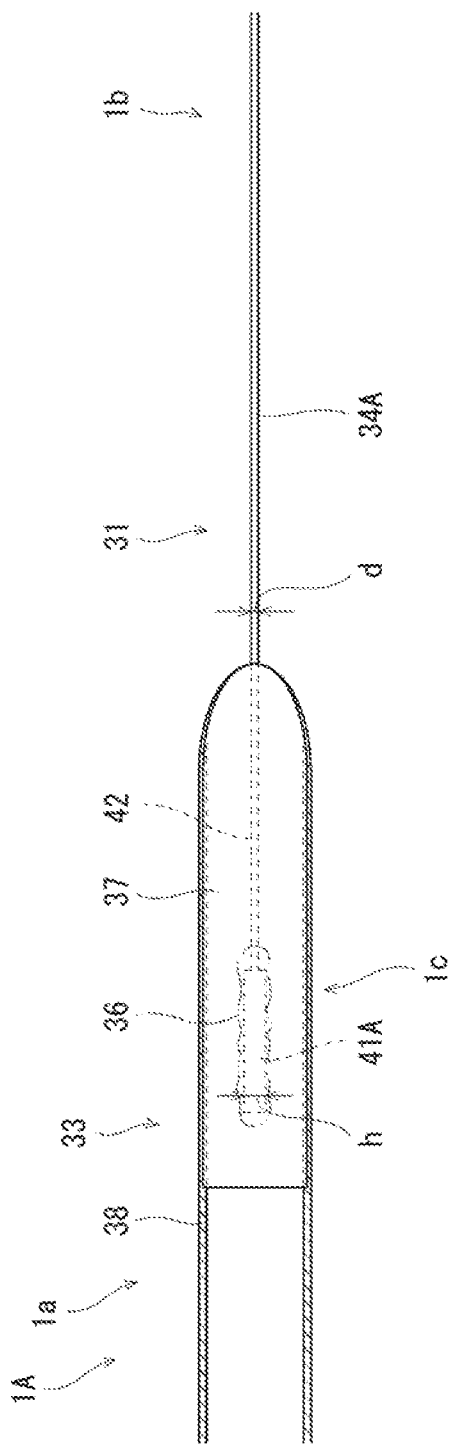
FIG. 4 is an enlarged bottom view of a joint portion where a proximal shaft and a distal shaft of a support catheter of Embodiment 2 of the present invention are joined together.

The support catheter 1A of Embodiment 2 includes a proximal shaft 34A as shown in FIG. 4. Similar to the proximal shaft 34 of Embodiment 1, the proximal shaft 34A is an elongated wire rod made of, for example, stainless steel, and the surface thereof is coated with PTFE. By flattening the distal end portion of the wire rod, a distal end portion 41A of the proximal shaft 34A is formed. That is, the distal end portion 41A of the proximal shaft 34A has a flat plate shape. To be more specific, the distal end portion 41A of the proximal shaft 34A is roughly rectangular when seen in a plan view. That is, the width of the distal end portion 41A is greater than the width of a remaining portion 42 of the proximal shaft 34A. The width h of the distal end portion 41A is, for example, not less than 1.5 times the diameter d of the remaining portion 42, but not more than 4 times the diameter d of the remaining portion 42. The remaining portion 42 is integrally joined to the center of one end of the distal end portion 41A in the longitudinal direction. From the one end of the distal end portion 41A in the longitudinal direction, the remaining portion 42 having an elongated linear shape protrudes toward one side in the lengthwise direction (i.e., toward the proximal end of the proximal shaft 34A).

Similar to the proximal shaft 34 of Embodiment 1, the distal end portion 41A of the proximal shaft 34A thus configured is disposed on the outer peripheral surface of the shaft body 35 so as to extend along the outer peripheral surface. That is, the entire distal end portion 41A is positioned on the outer peripheral surface of the shaft body 35. The adhesive 36 is applied to (placed on) the entire surface of the distal end portion 41A on the shaft body 35 side, and the distal end portion 41A is fixed (joined) to the outer peripheral surface of the shaft body 35 by the adhesive 36. In this manner, the adhesive area when the proximal shaft 34A and the shaft body 35 are fixed together can be increased, and thereby the adhesion strength can be increased. That is, the area of contact between the proximal shaft 34A and the distal shaft 33 is increased, and thereby the proximal shaft 34A can be more firmly fixed to the distal shaft 33.

<Durability Test>

A tensile durability test similar to that performed on the support catheter 1 of Embodiment 1 was performed on the support catheter 1A. That is, in the tensile durability test, the distal end of the support catheter 1A was held, and also, a part of the proximal shaft 34A was held. The part of the proximal shaft 34A was away from the distal end of the support catheter 1A by a predetermined length. In this state, pulling was repeatedly performed at a predetermined speed (e.g., 500 mm/min) with a predetermined load (e.g., not greater than 15 N), and the durability was evaluated. In the tensile durability test of the support catheter 1A, similar to the support catheter 1 of Embodiment 1, the support catheter 1A did not rupture even after the pushing and pulling was repeated 30 times. After it was repeated 30 times, the length of detachment of each of the proximal shaft 34 and the proximal shaft 34A from the distal shaft 33 (i.e., the amount of displacement of each of the proximal shaft 34 and the proximal shaft 34A relative to the distal shaft 33) was as follows. For example, the length of detachment in the support catheter 1 of Embodiment 1 was about 11 mm, whereas the length of detachment in the support catheter 1A of Embodiment 2 was about 3 mm. Thus, the support catheter 1A of Embodiment 2 has higher durability than the support catheter 1 of Embodiment 1.

In addition to the tensile durability test, another tensile test was performed on the support catheters 1 and 1A of Embodiments 1 and 2. In the tensile test, the distal-side portion of the support catheter 1 and the distal-side portion of the support catheter 1A were held, and also, a part of the proximal shaft 34 and a part of the proximal shaft 34A were held. The part of the proximal shaft 34 was away from the distal-side portion of the support catheter 1 by a predetermined length, and the part of the proximal shaft 34A was away from the distal-side portion of the support catheter 1A by the predetermined length. In this state, pulling was performed at a predetermined speed (e.g., 500 mm/min) with a gradually increased load, and a load value at which each catheter broke (i.e., the breaking strength of each catheter) was measured. The breaking strength of the support catheter 1 of Embodiment 1 was about 20 N, whereas the breaking strength of the support catheter 1A was about 25 N. That is, the support catheter 1A has higher breaking strength and is less likely to break than the support catheter 1 of Embodiment 1.

In addition, the support catheter 1A of Embodiment 2 provides the same functional advantages as those of the support catheter 1 of Embodiment 1.

Embodiment 3

A support catheter 1B of Embodiment 3 is similar in configuration to the support catheter 1A of Embodiment 2. Therefore, the description below regarding the configuration of the support catheter 1B of Embodiment 3 mainly describes differences from the configuration of the support catheter 1A of Embodiment 2. In Embodiment 3, the same configurations as those of Embodiment 2 are denoted by the same reference signs as those used in Embodiment 2, and the description and illustration of such configurations are omitted.

Figure 5:
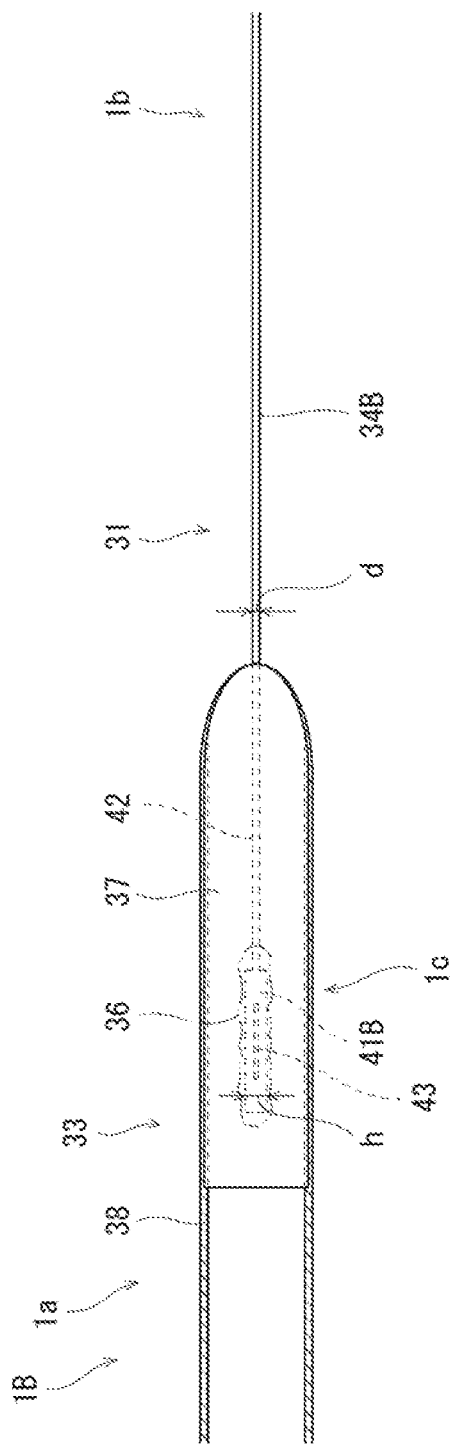
FIG. 5 is an enlarged bottom view of a joint portion where a proximal shaft and a distal shaft of a support catheter of Embodiment 3 of the present invention are joined together.

The support catheter 1B of Embodiment 3 includes a proximal shaft 34B as shown in FIG. 5, and a distal end portion 41B of the proximal shaft 34B has the following shape. Specifically, the distal end portion 41B of the proximal shaft 34B includes a through-hole 43, which extends through the distal end portion 41B in the thickness direction thereof. The through-hole 43 is formed at the center of the distal end portion 41B in the width direction thereof, and is elongated in the longitudinal direction of the distal end portion 41B. Similar to the proximal shaft 34A of Embodiment 2, the distal end portion 41B of the proximal shaft 34B having such a shape is disposed on the outer peripheral surface of the shaft body 35 so as to extend along the outer peripheral surface. That is, the entire distal end portion 41B is positioned on the outer peripheral surface of the shaft body 35. The adhesive 36 is applied to (placed on) the entire surface of the distal end portion 41B on the shaft body 35 side, and the distal end portion 41A is fixed (joined) to the outer peripheral surface of the shaft body 35 by the adhesive 36.

The adhesive 36 is applied to the distal end portion 41B in such an amount that when the distal end portion 41B is fixed to the outer peripheral surface of the shaft body 35, the through-hole 43 will be filled with the adhesive 36. The adhesive applied in such a manner flows into the through-hole 43, and is eventually solidified. Consequently, the through-hole 43 is filled with the solidified adhesive 36. As a result of the adhesive 36 being solidified in the through-hole 43, the following advantageous effect is obtained. Specifically, when the proximal shaft 34B is pushed and pulled, the adhesive 36, which has flowed into the through-hole 43 and has been solidified therein, is caught on the inner peripheral edge of the distal end portion 41B. This makes it possible to suppress displacement of the proximal shaft 34B relative to the distal shaft 33. That is, the length of detachment of the proximal shaft 34B from the distal shaft 33 can be reduced, and thus separation of the proximal shaft 34B from the distal shaft 33 can be suppressed. Since the through-hole 43 is elongated in the longitudinal direction of the distal end portion 41B, the adhesion strength of the adhesive 36 solidified in the through-hole 43 can be increased, and thereby the length of detachment of the proximal shaft 34B from the distal shaft 33 can be further reduced.

In addition, the support catheter 1B of Embodiment 3 provides the same functional advantages as those of the support catheter 1A of Embodiment 2.

OTHER EMBODIMENTS

As a technique in which the support catheters 1, 1A, and 1B of Embodiments 1 to 3 are used, the above description mainly describes a method of approaching a treatment site from a radial artery in PCI. However, as an alternative, the technique in which the support catheters 1, 1A, and 1B of Embodiments 1 to 3 are used may be a method of approaching a treatment site from a femoral region in PCI, the method being modeled in the above modeling test. The technique in which the support catheters 1, 1A, and 1B are used is not particularly limited. In each of the support catheters 1, 1A, and 1B, the stent 24 is externally fitted to the balloon 23. However, it is not essential to externally fit the stent 24 to the balloon 23. Also, the treatment catheter is not limited to the balloon catheter 5, but may be a different catheter, such as a Rotablator (RA) catheter or a directional coronary atherectomy (DCA) catheter.

The distal shaft 33 of each of the support catheters 1, 1A, and 1B need not have a three-layer structure, but may have a monolayer structure, a two-layer structure, or a multilayer structure having four or more layers. The materials forming the distal shaft 33 and the proximal shafts 34, 34A, and 34B of the support catheters 1, 1A, and 1B are not limited to the aforementioned materials. The materials forming the distal shaft 33 and the proximal shafts 34, 34A, and 34B of the support catheters 1, 1A, and 1B may be any suitable materials, so long as the adhesive 36 is an organic adhesive by which the material forming the shaft body 35 and the material forming the proximal shaft 34 can be adhered together. It should be noted that in the case of using a modified polyolefin-based adhesive as the adhesive 36, the drying time of the adhesive is short, which allows quick adhesion. Therefore, the use of a modified polyolefin-based adhesive facilitates the manufacturing of the support catheter 1.

Each of the support catheters 1, 1A, and 1B of Embodiments 1 to 3 includes the cover tube 37 and the cover shaft 38. However, it is not essential that each of these catheters include the cover tube 37 and the cover shaft 38. That is, the distal end portion 41, 41A, or 41B of the proximal shaft 34 may be fixed to the outer peripheral surface of the proximal-side portion of the distal shaft 33 solely by the adhesive 36. The distal end portion 41 of the proximal shaft 34 of Embodiment 1 need not be hook-shaped, but may have a different shape, such as an L shape or a linear shape. Also, the distal end portions 41A and 41B of the proximal shafts 34A and 34B of Embodiments 2 and 3 need not have a flat rectangular shape, but may have a polygonal or round shape. In Embodiment 3, a through-hole elongated in the longitudinal direction is formed in the distal end portion 41B of the proximal shaft 34B. However, it is not essential that the through-hole be an elongated through-hole. The through-hole may have any shape.

It is not essential that each of the distal end portions 41, 41A, and 41B of the proximal shafts 34, 34A, and 34B be fixed to the outer peripheral surface of the distal shaft 33. Alternatively, in a case where the distal shaft 33 is made up of a plurality of layers, the distal end portion 41, 41A, or 41B may be inserted between two layers of the distal shaft 33, and may be fixed between these two layers by an adhesive. Further alternatively, the distal end portion 41, 41A, or 41B may be fixed to the inner peripheral surface of the distal shaft 33 by an adhesive.

REFERENCE CHARACTERS LIST 1, 1A, 1B support catheter
1a distal-side portion
1b proximal-side portion
3 stenosis site (treatment site)
4 guiding catheter
4b proximal-side opening
5 balloon catheter
8 radial artery (blood vessel)
9 aortic arch (blood vessel)
23 balloon (distal end portion of a treatment catheter)
33 distal shaft
34, 33A, 34B proximal shaft
36 adhesive
37 cover tube
41 distal end portion
43 through-hole

The invention claimed is:

1. A support catheter used together with a guiding catheter in which a treatment catheter is inserted, the guiding catheter guiding the treatment catheter in a blood vessel, the support catheter being insertable in the guiding catheter from a proximal-side opening of the guiding catheter and having such a length that the support catheter protrudes from a distal-side opening of the guiding catheter, the support catheter guiding a distal end portion of the treatment catheter to a treatment site, the support catheter comprising:
a distal shaft forming a distal-side portion of the support catheter, the distal shaft having a tubular shape such that the treatment catheter is insertable in the distal shaft; and
a proximal shaft being an elongated wire rod forming a proximal-side portion of the support catheter, wherein
the distal shaft includes a shaft body and a cover tube,
a distal end portion of the proximal shaft is sandwiched between the shaft body and the cover tube, and
the distal end portion of the proximal shaft is joined to an outer peripheral surface of a proximal-side portion of the shaft body by a modified polyolefin-based adhesive that is applied to the distal end portion of the proximal shaft and to only part of a circumference of the outer peripheral surface of the proximal-side portion of the shaft body that is adjacent to the distal end portion of the proximal shaft.

2. The support catheter according to claim 1, wherein the proximal shaft is made of stainless steel, and the outer peripheral surface of the proximal-side portion of the shaft body is made of a polyamide resin.

3. The support catheter according to claim 1, wherein
the modified polyolefin-based adhesive is placed on the distal end portion of the proximal shaft, and
the distal end portion of the proximal shaft is bent back to be hook-shaped, and is thereby fixed to the outer peripheral surface of the proximal-side portion of the shaft body by the modified polyolefin-based adhesive.

4. The support catheter according to claim 1, comprising a cover shaft configured to cover an outer peripheral surface of the cover tube together with the distal end portion of the proximal shaft.

5. The support catheter according to claim 1, wherein
the modified polyolefin-based adhesive is placed on the distal end portion of the proximal shaft, and
the distal end portion of the proximal shaft has a flat plate shape such that a width of the distal end portion of the proximal shaft is greater than a width of a remaining portion of the proximal shaft, and the distal end portion of the proximal shaft is fixed to the outer peripheral surface of the proximal-side portion of the shaft body by the modified polyolefin-based adhesive in a state where the distal end portion of the proximal shaft is in contact with the outer peripheral surface of the proximal-side portion of the shaft body.

6. The support catheter according to claim 5, wherein the distal end portion of the proximal shaft includes a through-hole that extends through the distal end portion of the proximal shaft in a thickness direction thereof, and the modified polyolefin-based adhesive is present in the through-hole.

\* \* \* \* \*